United States Patent
Carey et al.

(10) Patent No.: US 7,448,248 B2
(45) Date of Patent: Nov. 11, 2008

(54) CALIBRATION AND VERIFICATION TOOL AND METHOD FOR CALIBRATING A DETECTION APPARATUS

(75) Inventors: Loucinda Carey, Londonderry, NH (US); Kurt Bistany, Methuen, MA (US)

(73) Assignee: GE Homeland Protection Inc., Newark, CA (US)

( * ) Notice: Subject to any disclaimer, the term of this patent is extended or adjusted under 35 U.S.C. 154(b) by 435 days.

(21) Appl. No.: 11/299,915

(22) Filed: Dec. 12, 2005

(65) Prior Publication Data

US 2007/0131017 A1    Jun. 14, 2007

(51) Int. Cl.
*G01N 33/00*    (2006.01)
(52) U.S. Cl. ......................... 73/1.04; 73/1.06
(58) Field of Classification Search ......... 73/1.02–1.04, 73/1.06; 436/8
See application file for complete search history.

(56) References Cited

U.S. PATENT DOCUMENTS

| | | | | |
|---|---|---|---|---|
| 3,977,798 | A | * 8/1976 | Kuparinen | 401/258 |
| 4,045,997 | A | 9/1977 | Showalter et al. | 73/23.2 |
| 4,202,200 | A | 5/1980 | Ellson | 73/31.05 |
| 4,772,794 | A | 9/1988 | Jenkins | 250/382 |
| 4,781,972 | A | 11/1988 | Sakane et al. | 442/146 |
| 4,807,979 | A | * 2/1989 | Saccomanno et al. | 359/368 |
| 4,896,547 | A | 1/1990 | Arney et al. | 73/863.81 |
| 4,964,309 | A | 10/1990 | Jenkins | 73/864.81 |
| 4,987,767 | A | 1/1991 | Corrigan et al. | 73/23.36 |
| 5,027,643 | A | 7/1991 | Jenkins | 73/23.39 |
| 5,109,691 | A | 5/1992 | Corrigan et al. | 73/23.36 |
| 5,200,614 | A | 4/1993 | Jenkins | 250/286 |
| 5,353,868 | A | * 10/1994 | Abbott | 165/171 |
| 5,360,412 | A | * 11/1994 | Nakao et al. | 604/247 |
| 5,405,781 | A | 4/1995 | Davies et al. | 436/52 |
| 5,425,263 | A | 6/1995 | Davies et al. | 73/28.06 |
| 5,491,337 | A | 2/1996 | Jenkins et al. | 250/287 |
| 5,585,575 | A | 12/1996 | Corrigan et al. | 73/863.71 |
| 5,741,984 | A | 4/1998 | Danylewych-May et al. | 73/864.71 |
| 5,753,832 | A | 5/1998 | Bromberg et al. | 73/864.81 |
| 5,760,314 | A | 6/1998 | Bromberg et al. | 73/863.21 |
| 5,859,362 | A | 1/1999 | Neudorfl et al. | 73/23.2 |
| 5,859,375 | A | 1/1999 | Danylewych-May et al. | 73/864.71 |
| 5,915,268 | A | 6/1999 | Linker et al. | 73/23.2 |
| 6,073,499 | A | 6/2000 | Settles | 73/864.81 |
| 6,334,365 | B1 | 1/2002 | Linker et al. | 73/864.81 |

(Continued)

OTHER PUBLICATIONS

"Discover the COPIC Difference"—Internet Article, Dec. 31, 2000, XP002427620, 1 page.

(Continued)

*Primary Examiner*—Thomas P Noland
(74) *Attorney, Agent, or Firm*—Global Patent Operation

(57) ABSTRACT

The calibration tool is provided for use with a detector, such as a detector for detecting trace amounts of one or more substances of interest. The calibration tool includes a body with at least one reservoir for retaining the calibration solution therein. A nib projects from the body and communicates with the reservoir. The nib can be wiped across a detection surface and the detection surface then may be presented to a detector. The detector then can be calibrated for the particular substance of interest in the calibration solution. The calibration tool may include plural reservoirs isolated from one another and plural nibs for applying the calibration solution to a detection surface.

13 Claims, 7 Drawing Sheets

U.S. PATENT DOCUMENTS

| | | | |
|---|---|---|---|
| 6,375,697 B2 | 4/2002 | Davies | 55/340 |
| 6,407,382 B1 | 6/2002 | Spangler | 250/286 |
| 6,642,513 B1 | 11/2003 | Jenkins et al. | 250/288 |
| 6,690,005 B2 | 2/2004 | Jenkins et al. | 250/287 |
| 6,831,273 B2 | 12/2004 | Jenkins et al. | 250/287 |
| 7,047,829 B2 * | 5/2006 | Napoli | 73/864.31 |
| 2004/0131503 A1 | 7/2004 | McGann et al. | 422/99 |
| 2005/0019220 A1 | 1/2005 | Napoli | 422/99 |
| 2005/0057354 A1 | 3/2005 | Jenkins et al. | 340/522 |

OTHER PUBLICATIONS

"Refilling COPIC Markers"—Internet Article, Dec. 31, 2000, XP002427621., 1 page.

"Standard Operating Procedure 011 Photoionization Detector" (HNu Model PI-101 and HW-101)-Pennington Judith C. et al., Technical Report EL-99-7, Jul. 31, 1996, XP002427622., pp. 1-5.

"Acute Toxicity of Marking Pen Emissions"—Rosalind Anderson and Julius Anderson, Journal of Toxicology and Environmental Health, Jun. 13, 2003, pp. 829-845, XP009081369.

* cited by examiner

CALIBRATION AND VERIFICATION TOOL AND METHOD FOR CALIBRATING A DETECTION APPARATUS

BACKGROUND OF THE INVENTION

1. Field of the Invention

The invention relates to calibration tools and methods for calibrating an apparatus that is used to test for the presence of trace amounts of substances of interest.

2. Description of the Related Art

Terrorism risks continue to increase at transportation facilities, government buildings, banks, restaurants, hotels and other locations where there is a significant flow of pedestrian or vehicular traffic. As a result, virtually all airports and many other buildings now include apparatus for detecting trace amounts of explosives.

Narcotics are illegal and insidious. Furthermore, it is known that many terrorists organizations fund their terrorism through the lucrative sale of narcotics. Accordingly, many airports and other public buildings recognize the need to check for narcotics.

U.S. Pat. No. 5,491,337 discloses a device that employs and ion trap mobility spectrometer to test for trace amounts of contraband. The ion trap mobility spectrometer can be operated in a negative mode to test for trace amounts of explosives. The ion trap mobility spectrometer disclosed in U.S. Pat. No. 5,491,337 also can be operated in a positive mode to check for trace amounts of narcotics. Additionally, the apparatus of U.S. Pat. No. 5,491,337 can be switched quickly from the positive mode to the negative mode so that a single sample can be tested for the presence of trace amounts of either explosives or narcotics. Detectors that incorporate the technology disclosed in U.S. Pat. No. 5,491,337 are marketed by GE Security, Inc. and perform very well. The disclosure of U.S. Pat. No. 5,491,337 is incorporated herein by reference.

Prior art detectors have used many techniques for delivering a sample into the detector to test the sample for substances of interest. For example, some detectors employ small flexible fabric-like traps that can be wiped across a package or piece of luggage. The trap removes residue from the surface of the package or luggage. The trap then is placed in an apparatus, such as an ion trap mobility spectrometer, that tests the residue on the trap for trace amounts of explosive materials or narcotics.

Detectors that rely upon wiping a flexible fabric trap across a piece of luggage impede the flow of pedestrians through a check point, and hence typically are used only for spot checks. Additionally, an explosive or narcotic detector of this type would not identify a contraband worn by a passenger or other pedestrian who was not carrying luggage.

U.S. Pat. No. 6,073,499 discloses a walk-through detector. The detector shown in U.S. Pat. No. 6,073,499 operates under the principle that a boundary layer of air adjacent to a person is heated by the person. This heated air adjacent a person is less dense than air further from the person. Less dense air rises. Accordingly, a thermal plume of air flows up adjacent to a person. Minute particles, including particles of explosives or narcotics, will be entrained in this thermal plume of air and will flow upwardly from a person. The walk-through detector disclosed in U.S. Pat. No. 6,073,499 employs an ion mobility spectrometer or ion trap mobility spectrometer to detect microscopic particles of interest that are likely to be entrained in the thermal plume of air flowing upwardly adjacent to a person who walks through and pauses briefly in the detector. The walk-through detector disclosed in U.S. Pat. No. 6,073, 499 is very effective for detecting whether a person is carrying explosives or narcotics and whether the person has recently handled explosives or narcotics. The disclosure of U.S. Pat. No. 6,073,499 is incorporated herein by reference.

The walk through detector of U.S. Pat. No. 6,073,499 is extremely effective and operates very quickly. However, the device is large and is not suitable for many access points.

Pending U.S. Patent Publication No. 2005/0019220 discloses a small detector with a slot through which a card may be swiped. This device operates under the theory that trace amounts of particles of interest will be transferred from the hand of a passenger or other pedestrian to the card. These trace amounts of particles of interest then are removed as the card is swiped through the slot and particles removed from the card can be analyzed to determine whether substances of interest are present. U.S. patent application No. 10/929,915 discloses another small detector apparatus that can be used quickly to detect for the presence of substances of interest. More particularly, the detector of U.S. patent application No. 10/929,915 includes a thin metal disc or a thin metal drum that rotates into proximity to a window. A passenger or other pedestrian who desires access places his or her fingers on the metal disc or drum. Residue from the fingers are transferred to the metal. The removal of the fingers from the metal disc or drum generates a signal that causes the area that had been contacted to move into the detector. The metal material is heated sufficiently to vaporize residue thereon and the vaporized residue is transported into the ion trap mobility spectrometer. The disclosures of U.S. Patent Publication No. 2005/0019220 and U.S. patent application No. 10/929,915 are incorporated herein by reference.

The above-described detectors work extremely well. However, variations in atmospheric pressure, humidity and temperature can affect the performance of these known detectors. For example, a detector used in Denver may function differently than a detector used in Florida. Furthermore, detectors used at any geographic location may perform differently from day-to-day as climactic conditions change. Therefore, it is necessary to calibrate the detectors periodically to ensure that the detectors function with sufficient accuracy to detect trace amounts of explosives or narcotics based on a very small sample size for the ambient conditions that exist on a particular day and at a particular location. Manufacturers of these detectors, such as GE Security, Inc., generally recommend calibration on a daily basis, such as at the start of every work day. Devices that wipe a fabric trap across an item of luggage are calibrated by using a calibration trap that is known to have small amounts of the substance of interest thereon or a substance that is known to have a very similar signature. This calibration trap could be stored in a sealed container that is kept near the detector apparatus for access by the security personnel. Calibration traps, however, are not particularly useful for the more recent detector devices that analyze residue on the fingers of a person who desires access.

In view of the above, it is an object of the subject invention to provide an inexpensive tool that can be used for calibrating a contraband detector so that the detector can accurately test for substances of interest.

SUMMARY OF THE INVENTION

The invention relates to a calibration tool for calibrating a detector that is operative for detecting small amounts of at least one substance of interest. The calibration tool includes a reservoir for retaining a calibration solution and a dispenser for dispensing small amounts of the calibration solution onto a region of the detector that will be tested for the presence of at least one substance of interest.

The reservoir of the calibration tool may be contained in a handle that is dimensioned to be held and manipulated easily by a user. The dispenser may include a wick that has one end in communication with the reservoir and another end exposed externally on the handle The tool further includes a closure for selectively isolating the dispenser and the reservoir within the handle to prevent excessive evaporation of the calibration solution in the reservoir. The closure is a removable cap in a preferred embodiment of the calibration tool. However, other closures can be provided, such as a slit that opens only in response to pressure, a spring actuated valve or a ball bearing that can rotate at the end of the tool for selectively transferring the calibration solution in much the same manner that a ball point pen dispenses ink to a sheet of paper. The reservoir can include a small plastic bladder that can be pierced during an initial use of the calibration tool. The bladder may be replaceable as needed.

The calibration solution in the reservoir may be a solution with at least one signature similar to the signature of at least one substance of interest. However, the calibration solution in the reservoir preferably is a diluted solution that includes the at least one substance of interest.

The detector may be operative for detecting the presence of explosives. In this situation, the calibration solution in the reservoir of the calibration tool may comprise a diluted solution of at least one known explosive, such as TNT, RDX or other known plastic or non-plastic explosive.

The detector may be operative for detecting the presence of at least one narcotic. In this situation, for example, the calibration solution in the reservoir of the calibration tool may comprise a diluted solution of cocaine or other known narcotic that will be tested for.

As noted above, some detectors are operative to test in more than one mode, and specifically, a negative ion mode and a positive ion mode. The negative mode typically is employed to test for the presence of explosives, while the positive mode is operative to detect for the presence of narcotics. The calibration tool may be configured for use with a dual mode detector, such as the detector described above and disclosed in U.S. Pat. No. 5,491,337. A calibration tool for a dual mode detector may have a calibration solution with two substances of interest.

The calibration tool may include first and second reservoirs and first and second dispensers that communicate respectively with the reservoirs. The first reservoir and the first dispenser are isolated from the second reservoir and the second dispenser. The first reservoir and first dispenser preferably are for calibration and the second reservoir and second dispenser preferably are for verification. For example, the calibration tool may include an elongate generally tubular body. The first and second reservoirs may be disposed in the body and may be separated from one another by at least one transverse wall. The first dispenser may be at a first longitudinal end of the body, while the second dispenser may be at the second longitudinal end of the body. The first reservoir preferably includes a calibration solution while the second reservoir preferably includes a verification solution. The calibration and verification solutions may be two different dilute solutions of substances of interest. For example the calibration tool for a single mode explosive detector may have a dilute solution of TNT in the first reservoir and a dilute solution of RDX in the second reservoir. A calibration tool for a dual mode detector may have a dilute solution of TNT and cocaine in the first reservoir and a dilute solution of RDX and Ephedrine in the second reservoir.

The calibration tool with two reservoirs and two dispensers may further include first and second closures for selectively closing the corresponding reservoirs and dispensers. The closures may be first and second caps or the other known closures described above, such as a slit valve, a rolling ball or the like. The closure also can be a spring biased valve that is normally biased towards a closed condition. Pressure exerted on the end of the dispenser may open the valve to permit small amounts of the calibration solution to be dispensed.

The calibration tool is used by removing or opening the closure and applying a small amount of the calibration solution to the sample collection region on the detector. The detector then is operated in a calibration mode and may be adjusted accordingly so that test parameters for the calibration solution are identified by the detector as being associated with the particular substance or substances of interest. The second dispenser of the calibration tool then may be used to apply a small amount of the verification solution to the sample collection region of the detector. The detector then may be operated to verify that the detector identifies the verification solution as having a different species of the substance or substances of interest. The detector then may be calibrated further based on the ability of the detector to detect the substance or substances of interest in the verification solution.

DETAILED DESCRIPTION OF THE PREFERRED EMBODIMENTS

The calibration tool of the subject invention is intended for use with a detector that is operative for detecting small amounts of substances of interest, and particularly trace amounts of substances of interest that may be transferred from the fingers of a person to a sample collection area of the detector. Detectors of this type are particularly effective for detecting trace amounts of explosives or narcotics. One example of such a detector is identified generally by the numeral 10 in FIG. 1.

The detector 10 includes an outer housing 11 and a flat panel display monitor 12, such as an LCD monitor. An ion trap mobility spectrometer (ITMS) is disposed within the housing 11 and is illustrated schematically in FIG. 2.

Figure 2:
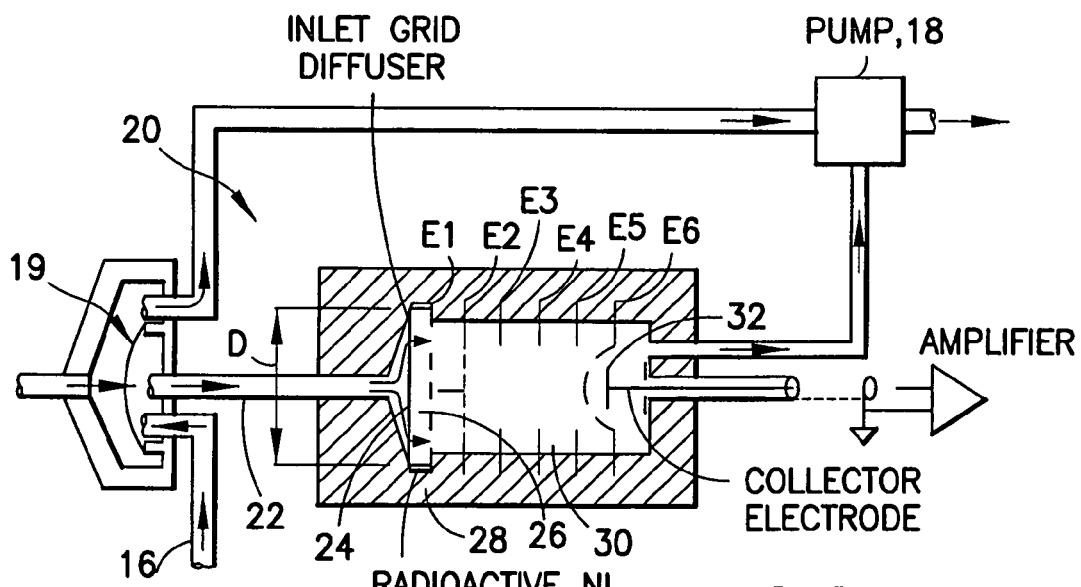
FIG. 2 is a schematic view of an ion trap mobility spectrometer of the detector shown in FIG. 1.

The ITMS of FIG. 2 comprises a cylindrical detector 20 having an inlet 22 at one end for receiving sample air of interest borne by a carrier gas which that has been doped with a low concentration vapor (typically a few parts per million) employed as a charge transfer mediator. More particularly, the inlet 22 communicates with a source of sample air of interest 14 and a supply of carrier gas and dopant 16 with flows of gases to the inlet 22 being enabled by a flow generator such as a pump illustrated schematically and identified by the numeral 18 in FIG. 2. A heated membrane 19 formed from a microporous refractory material or from dimethyl silicone is disposed near the inlet 22 and in communication with the source of the sample of air 14 for blocking passage of at least selected constituents of the air and for enabling passage of other constituents of the air, including the constituents of interest. The sample air, carrier gas, and dopant molecules pass through the inlet 22 and are spread by a diffuser 24 into an ionization chamber 26. The ionization chamber 26 is in the form of a shallow cylinder with a diameter D, length L, and cylindrical wall 28 of a radioactive material, e.g., nickel$^{63}$ or tritium, which emits beta particles. Inlet 22 communicates with one end of the ionization chamber 26. A grid electrode $E_1$ is provided at the end opposite the inlet 22, and is normally maintained at the same potential as the inlet end and the walls of the ionization chamber 26. Thus a largely field-free space is provided in which electrons and ion charges build up and interact with the sample molecules under bombardment by the beta-particles from the radioactive walls. Beyond the ionization chamber 26, the ionized sample gases pass through open electrode $E_1$ and into an ion drift region 30 having several field-defining electrodes $E_2$-$E_n$. A collector electrode or plate 32 is disposed at the end of the drift region 30 for receiving the ion samples reaching that end.

Periodically a field is established across the ionization region 26, by creating a potential difference between the grid electrode $E_1$ and the inlet diffuser 24 and radioactive source 28, for about 0.1-0.2 mS, to sweep the ions through the open grid $E_1$ into the drift region 30 with the assistance of the switching of the field between electrodes $E_1$ and $E_2$. The ions in the drift region 30 experience a constant electric field, maintained by the annular electrodes $E_2$-$E_n$, impelling them along the region and down toward the collector electrode 32. The electrode 32 detects the arriving charge, and produces signals that are amplified and analyzed through their spectra in the spectrometer. The gases exit through an outlet in the wall next to the electrode 32. After about 0.2 mS the field across the ionization region 26 is again reduced to zero and the ion population is again allowed to build up in the chamber 26 preparatory to the imposition of the next field. The polarity of the fields is chosen on the basis of whether the detector is operated in a negative or positive ion mode. When detecting explosives, a negative ion mode is usually appropriate, but when detecting narcotic samples positive ion mode is preferred. The two modes can be operated in rapid sequence to test a single sample for both explosive and narcotics.

Figure 1:
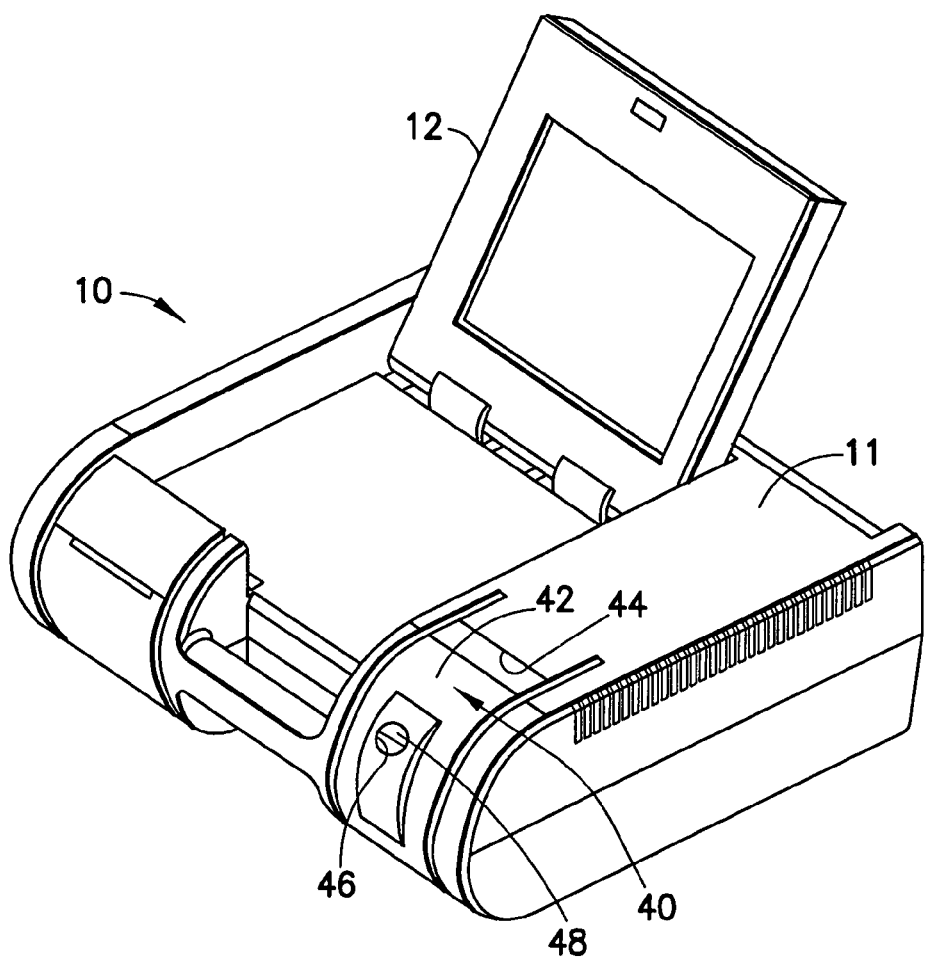
FIG. 1 is a perspective view of a detector that can be used with the calibration tool of the subject invention.
Figure 3:
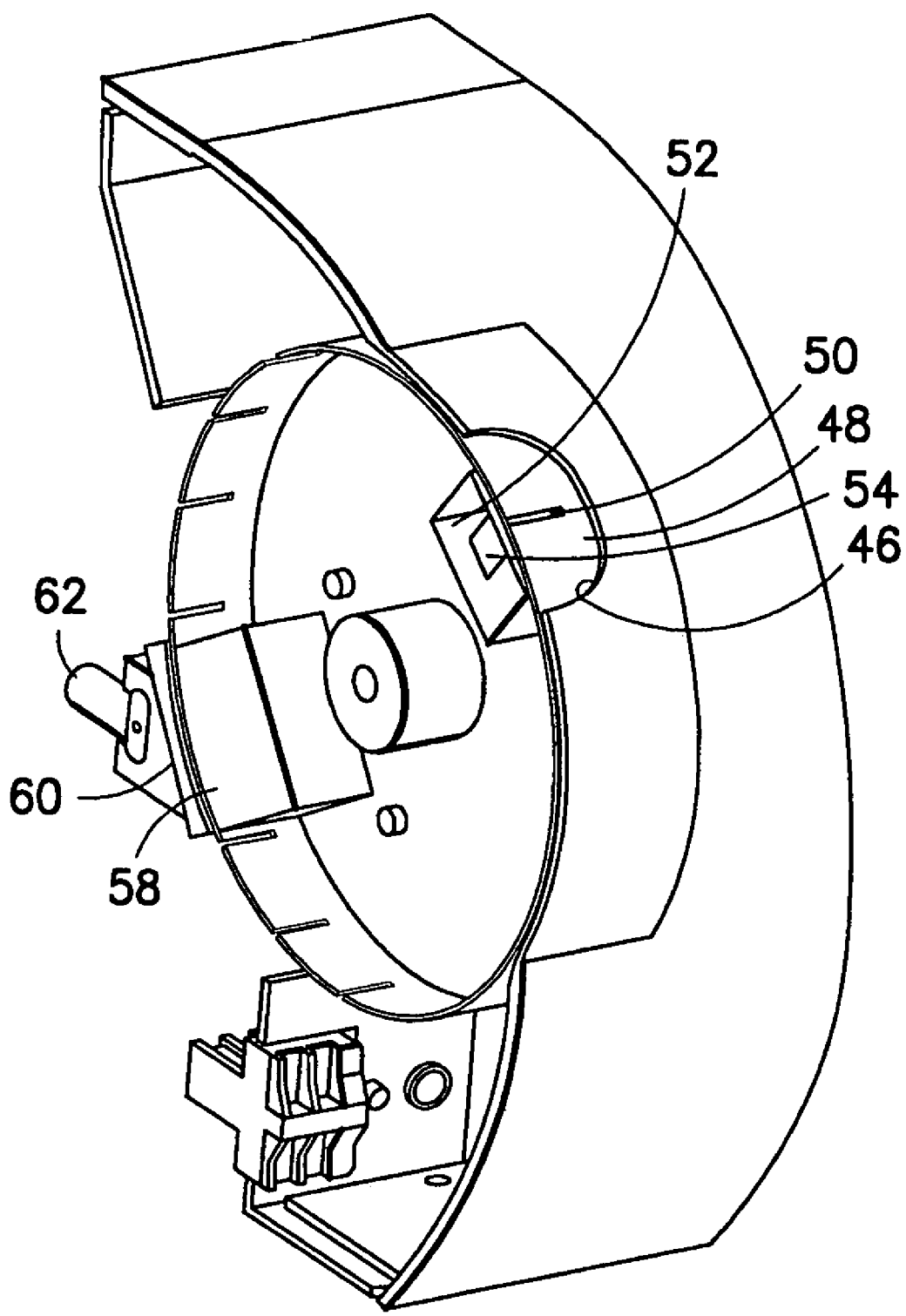
FIG. 3 is a front perspective view, partly in section, of a sample collection assembly of the detector for detecting substances of interest on a finger of a person.

The detector 10 includes a sample collection apparatus that is identified generally by the numeral 40 in FIGS. 1 and 3. The sample collection apparatus 40 includes a housing 42 and a window 46 at a position on the housing 42 that will face the person that is to be scanned for trace amounts of substances of interest. The window 46 is configured and dimensioned to receive at least part of the gripping surface of a thumb or forefinger.

The sample collection apparatus 40 further includes a generally cylindrical drum 48 mounted in the housing 42 for rotation about an axis that is parallel to the front face of the detector 10. More particularly, the cylindrical drum 48 is disposed to be substantially internally tangent with portions of the housing 42 adjacent the window 46. Hence, a target area on the exterior of the drum 48 will be exposed at the window 46. The drum 48 is formed from a material that will retain residue from the hand of a person being screened. The material of the drum 48 also must be able to be heated quickly and repeatedly to sufficiently high temperatures for vaporizing residue received from the hand. Additionally, the material of the drum 48 should be capable of being cooled quickly to prevent discomfort when a finger is placed on the drum 48 and to maintain a desirably low cycle time for scanning. The material of the drum preferably is a thin metallic material, such as aluminum or stainless steel. The thickness of the material of the drum 48 is selected to facilitate rapid heating and cooling, and to permit slight inward deflection of the drum 48 in response to digital pressure created by a thumb or forefinger placed on or wiped across the target area of the drum 48 exposed at the window 46. This deflection can trigger a pressure sensitive switch 52 to activate a scanning cycle.

The sample collection apparatus 40 further includes a motor 56 mounted to the housing and operative to rotate the drum 48. The motor 56 is connected to the switch 52 and functions to rotate the drum 48 a selected amount in response to the sensed completion of a wipe of a thumb or forefinger across portions of the drum 48 disposed in the window 46.

A desorber 58 is mounted to the housing 42 interiorly of and adjacent to the drum 48. The desorber 58 rapidly heats portions of the drum 48 for vaporizing trace amounts of material transferred from the thumb or forefinger to the target area of the drum 48 that was exposed at the window 46. A sample transfer box 60 is mounted to the housing 42 at a location radially aligned with the desorber 58, but disposed exteriorly of and substantially adjacent the drum 48. The sample transfer box 60 further includes a sample tube 62 that communicates with the inlet 22 of the ion trap mobility spectrometer of FIG. 2.

The movement of a thumb across the target area of the drum 48 exposed at the window 46 will deflect the thin aluminum of the drum 48 and will actuate the pressure sensitive switch 52 aligned with the window 46. The switch 52 will cause the motor 56 to rotate the drum 48. Thus, the target area of the drum 48 that had been aligned with the window 46 will advance into the narrow space between the desorber 58 and the sample transfer box 60. The motor 56 then stops. The heated desorber 58 raises the temperature of the drum 48 between the desorber 58 and the sample transfer box 60 sufficiently to vaporize residue transferred from the thumb to the drum 48. A vacuum pump 18 in the detector of FIG. 2 then will draw the vaporized material through the sample collection tube 62 and into the detector for analysis. The ITMS will detect the presence of substances of interest and will generate an appropriate signal for additional or enhanced testing by security personnel at the checkpoint.

Figure 4:
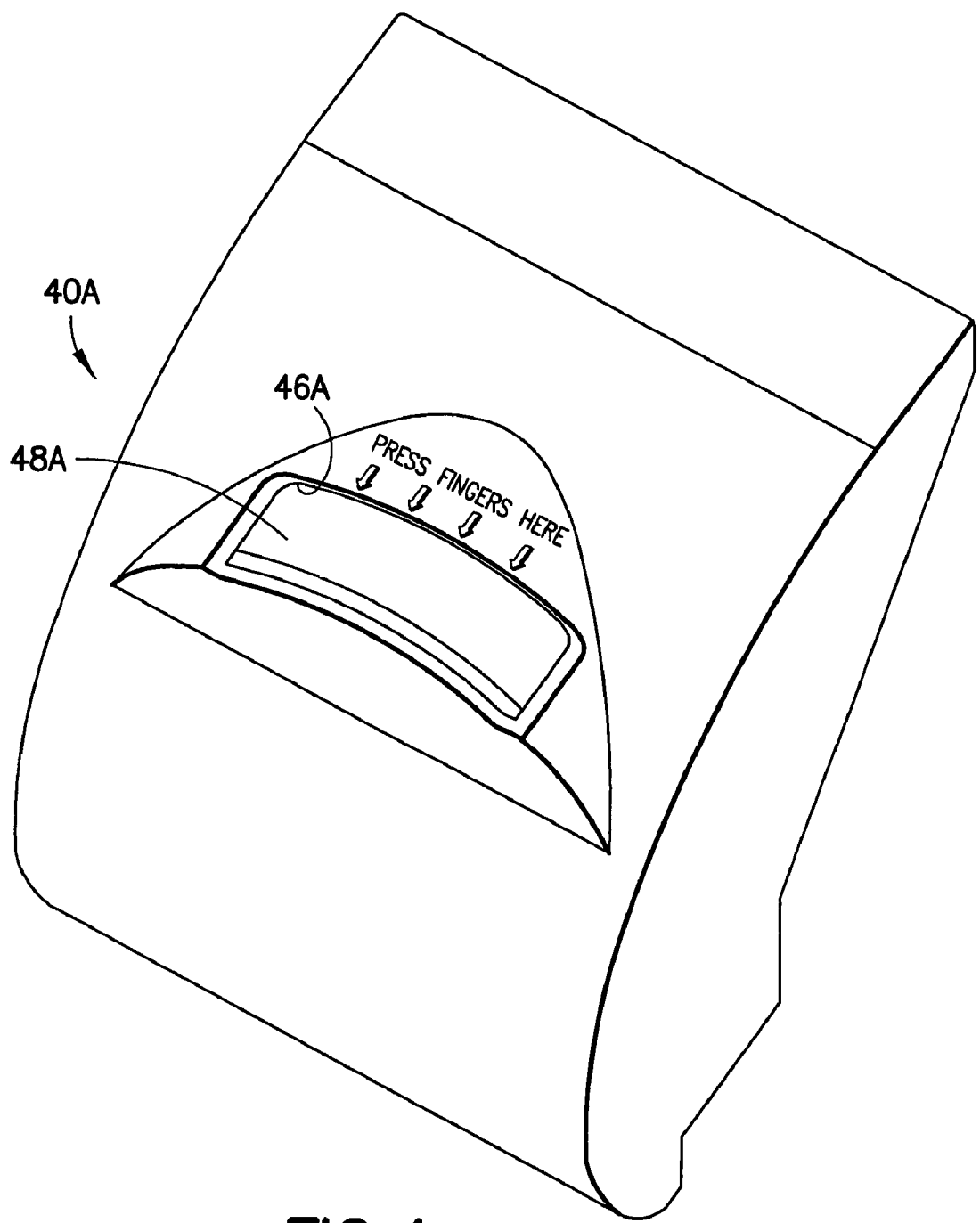
FIG. 4 is a perspective view of an alternate sample collection assembly that can be used with the calibration tool of the subject invention.
Figure 5:
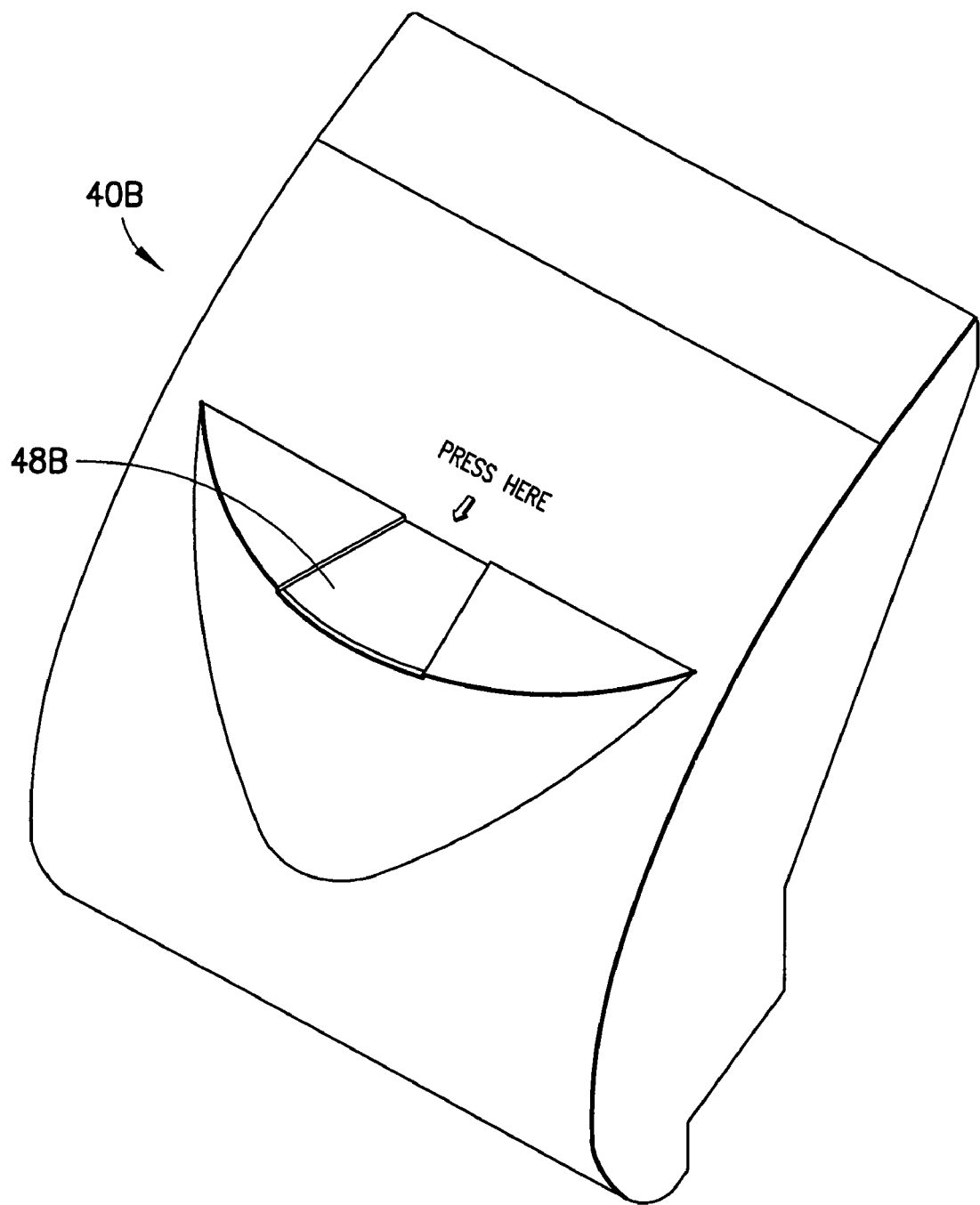
FIG. 5 is a perspective view of another alternate sample collection assembly that can be used with the calibration tool of the subject invention.
Figure 6:
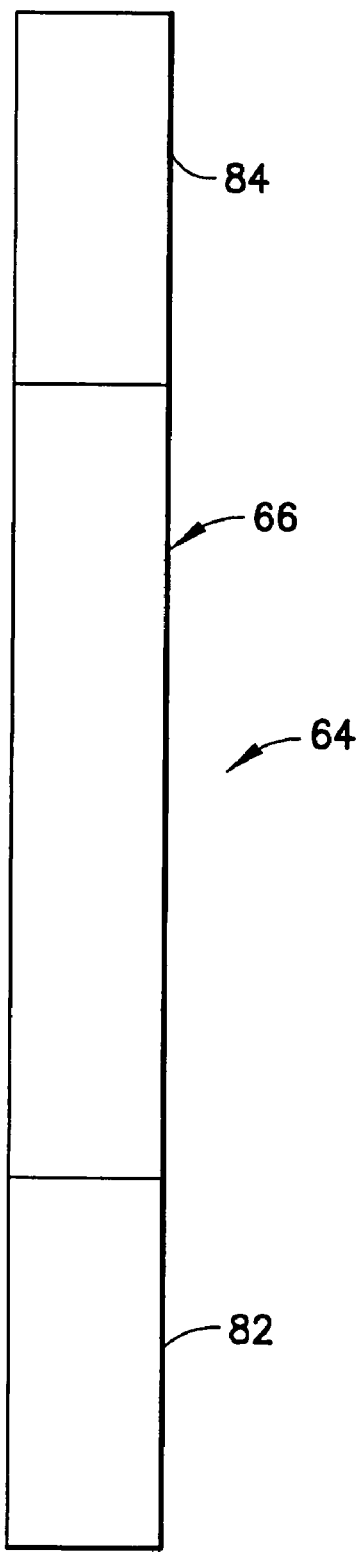
FIG. 6 is a perspective view of one embodiment of a calibration tool in accordance with the subject invention.

The sample collection apparatus can take other configurations. For example, FIG. 4 shows a sample collection apparatus 40A with a drum 48A mounted for rotation about an axis aligned at an angle, and preferably a right angle, to the front face of the detector 10. The window 46A is sufficiently wide to place all forefingers of one hand on a portion of the drum 48A exposed at the window. FIG. 5 shows a detector 40B with an aluminum disc 48B in place of the drum. The disc 48B rotates about a substantially vertical axis. Other options can include a thin plate that translates without rotation or a flexible belt that is driven about rollers.

The detector 10 must be calibrated periodically to ensure that the detector 10 will associate certain sensed peaks with certain substances of interest under the current conditions of temperature, atmospheric pressure and humidity at the detection site. Accordingly, the detector may be used with a calibration tool identified generally by the numeral 64 in FIGS.

Figure 7:
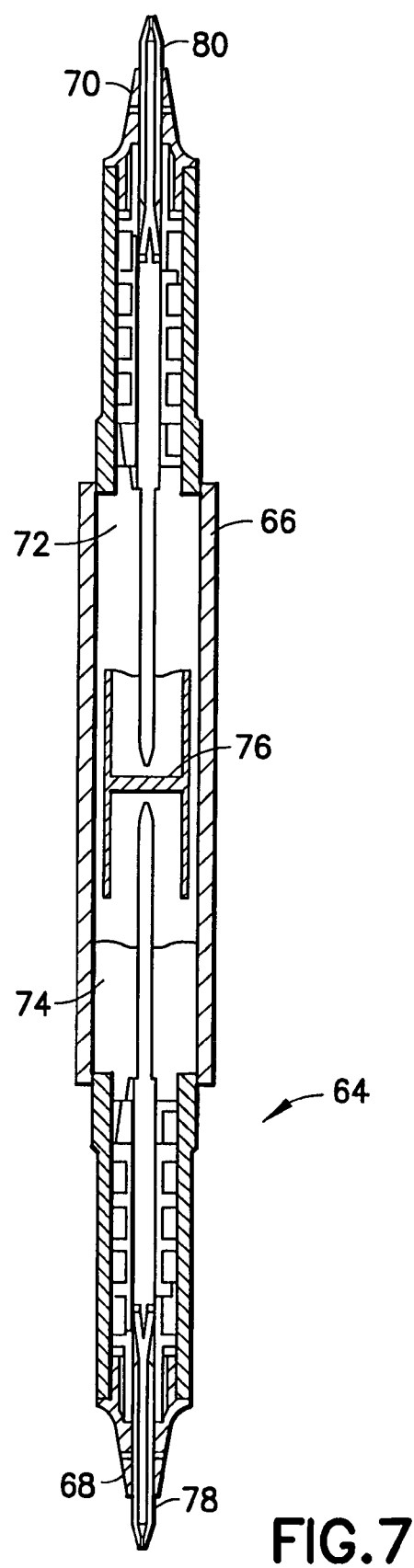
FIG. 7 is a longitudinal cross-sectional view of the calibration tool of FIG. 6 with the caps thereof removed.
Figure 8:
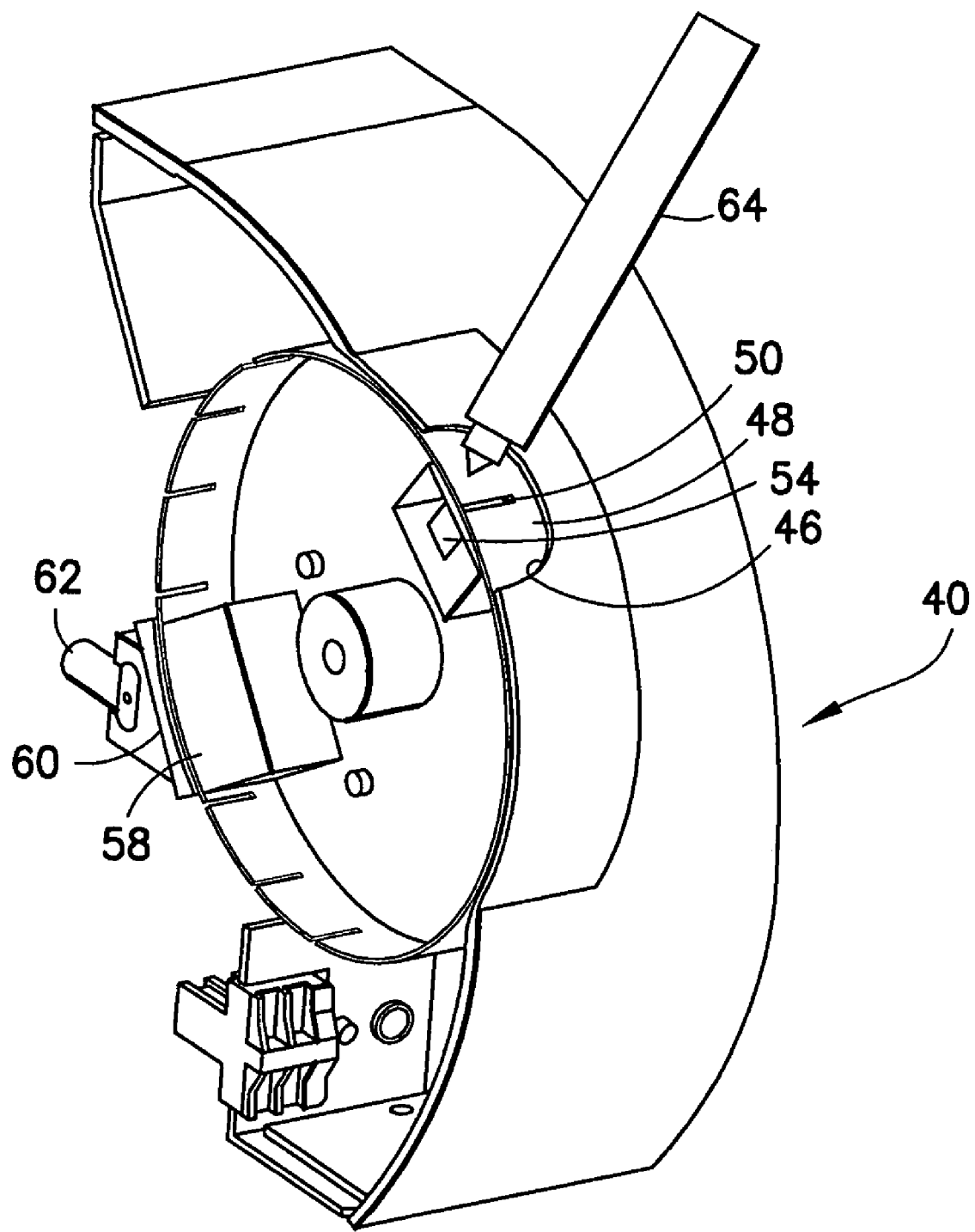
FIG. 8 is a schematic perspective view showing the calibration tool used with a detector of the type shown generally in FIGS. 1 and 2.

6-8. The calibration tool 64 includes an elongate body 66 having opposite first and seconds ends 68 and 70. As shown most clearly in FIG. 7, first and second reservoirs 72 and 74 are formed inside the body 66 and are isolated from one another by a transverse wall 76. A calibration solution is disposed in the first reservoir 72 and a verification solution is disposed in the second reservoir 74. A first marker nib 78 is formed in proximity to the first end 68 of the body 66 and communicates with the first reservoir 72. A second marker nib 80 is formed in proximity to the second end 70 of the body 66 and communicates with the second reservoir 74. First and second caps 82 and 84 are mounted removably to the first and second ends 68 and 70 of the body 66 for covering the first and second nibs 78 and 80 respectively. FIG. 7 shows an embodiment where valves are disposed in the body for selectively placing the nibs 78 and 80 in communication with the reservoir 72 and 74. The valves normally are biased towards a closed position, but can be opened in response to pressure exerted on the nibs 78 or 80 during normal use of one end of the tool 64. However, other means for delivering solution from the reservoir 72 or 74 to the nibs 78 or 80 can be provided, including a simple felt or foam wick that extends from the reservoirs 72, 74 to the nibs 78, 80. COPIC markers distributed by Imagination International, Inc. have proved very successful for the calibration tool 64. In this regard, COPIC markers can be purchased empty and filled or refilled with appropriate calibration solutions.

The calibration and verification solutions preferably are in liquid form and are selected to produce a signature that will be recognized by the detector 10 as one of the substances of interest. In this regard, a preferred calibration solution is a dilute solution of TNT and cocaine in the first reservoir 72. More particularly, the preferred solvent is alcohol and most preferably methanol. The TNT and cocaine preferably are present in the calibration solution at concentrations of about 100 nanograms of TNT and about 100 nanograms of cocaine per microliter of solution. The verification solution preferably includes RDX and a second narcotic of interest (e.g., Ephedrine) in the second reservoir 74. The verification solution preferably has about 50 nanograms of RDX and about 250 nanograms of Ephedrine per microliter of solution. The solvent for the verification solution may be the same as the solvent for the calibration solution.

The calibration tool 64 is used by removing the first cap 82 to expose the first nib 78 of the calibration tool 64. The first nib 78 is wiped across or pressed on the surface of a sample collection apparatus 40 exposed at the window 46 of the detector 10 to apply a small amount of the calibration solution. Removal of the calibration tool 64 from the sample detection surface will activate the pressure sensitive switch 52 and cause the detector 10 to proceed through a detection or calibration cycle. The calibration solution containing a selected explosive (e.g., TNT) and the selected narcotic (e.g., cocaine) will generate signal spikes for a specified peak time and peak height that permits the detector 10 to be calibrated for the explosive and narcotics in the calibration solution based on the ambient temperature, atmospheric pressure and humidity at the particular time and at the particular test location. The first cap 82 then is placed back on the body 66 to cover the first nib 78. The second cap 84 then can be removed from the body 66 to expose the second nib 80. The second nib 80 then can be pressed against or wiped across the detection surface to deposit a small amount of the verification solution that contains a second explosive (e.g., RDX) and a second narcotic (e.g., Ephedrine). The detector then is operated to verify that the detector identifies the substances of interest in the verification solution. Further calibration can be performed if necessary.

While the invention has been described with respect to a preferred embodiment, it is apparent that various changes can be made without departing from the scope of the invention as defined by the appended claims. For example, the figures herein show one particular configuration for a calibration tool with a valve between the outlet of the reservoir and exterior portions of the nib. However, many other configurations can be provided for the calibration tool, including felt tip markers with no valves. Many of the commercially available markers, highlighters or the like can be used provided that there is some protection against evaporation (e.g., a valve or cap) and some protection against excessive leakage for the particular selected viscosity of the calibration solution.

A dual-ended calibration tool is illustrated. However, a calibration tool with a single marker can be provided.

A few examples of specific calibration and verification solutions were identified based on typical intended uses for the detectors. However, other calibration and/or verification solutions can be employed in accordance with the specific application of the detector. The concentration of the substances of interest in the solution also can be varied considerably in accordance with the sensitivity of the detector. Thus, less concentrated calibration solutions can be employed for a detector, such as an ion trap mobility spectrometer, that can detect trace amounts of a substance of interest.

The calibration tool is illustrated for use with a particular detector. However, the calibration tool can be used with other detectors.

The calibration tool is particularly preferable for use with a detector where a passenger or other person being screened wipes his or her finger across a detection surface that is to be analyzed. However, the calibration tool also can be used with a detector that employs sample traps or cards. In this regard, the nib of the calibration tool can be wiped across an initially clean sample trap or card that then is presented to the detector for analysis.

These and other variations will be apparent to a person skilled in the art after having read the subject invention disclosure and the accompanying drawings.

What is claimed is:

1. A calibration tool for calibrating a detector that is operative for detecting whether at least one substance of interest is present in or on a sample, the calibration tool comprising:

at least one reservoir containing a selected solution with at least one substance of interest therein; and at least one nib communicating with the reservoir for applying a portion of the solution to a detecting surface of the detector.

2. The calibration tool of claim 1, wherein the solution contains an explosive material.

3. The calibration tool of claim 2, wherein the solution further contains a narcotic material.

4. The calibration tool of claim 1, wherein the solution contains a narcotic material.

5. The calibration tool of claim 1, wherein the at least one reservoir comprises first and second reservoirs isolated from one another and wherein the at least one nib comprises first and second nibs communicating respectively with the first and second reservoirs.

6. The calibration tool of claim 5, wherein the tool includes an elongate body, the first and second reservoirs being disposed in the body, the first and second nibs being disposed at opposite respective ends of the elongate body.

7. The calibration tool of claim 6, further comprising first and second caps secured removably to the body for selectively covering the first and second nibs respectively.

8. The calibration tool of claim 5, wherein the first reservoir includes a calibration solution containing a first explosive material and a first narcotic therein and wherein the second reservoir includes a verification solution containing a second explosive material and a second narcotic therein.

9. The calibration tool of claim 1, wherein the substance of interest is present in the solution with a concentration of about 50-250 nanograms per microliter of solution.

10. A method for calibrating a detector that is used for detecting trace amounts of at least a first substance of interest, the method comprising:
    providing a marker with a calibration reservoir that contains a calibration solution with a first species of the first substance of interest, the marker further having a calibration nib communicating with the calibration reservoir and positioned to be exposed at an external position on the calibration tool;
    urging the calibration nib against a detection surface of the detector so that a portion of the calibration solution in the calibration reservoir is applied to the detection surface; and
    operating the detector for calibrating the detector to the first substance of interest in the calibration solution.

11. The method of claim 10, wherein the marker further has a verification reservoir that contains a verification solution that has at least a second species of the at least one substance of interest, the marker further having a verification nib communicating with the verification reservoir and positioned to be exposed at an external position on the calibration tool, the method further comprising:
    urging the verification nib against the detection surface of the detector so that a portion of the verification solution in the verification reservoir is applied to the detection surface; and
    operating the detector for verifying that the detector can identify the second species of the at least one substance of interest in the verification solution.

12. The method of claim 11, wherein the calibration reservoir further contains a first species of a second substance of interest, the step of urging the calibration nib against the detection surface substantially simultaneously applies the first species of the first substance of interest and the first species of the second substance of interest to the detection surface and wherein the step of operating the detector is carried out for calibrating the detector to the first substance of interest and the second substance of interest in the calibration solution.

13. The method of claim 12, wherein the verification solution further includes a second species of the second substance of interest, the step of urging the verification nib against the detection surface substantially simultaneously applies the second species of the first substance of interest and the second species of the second substance of interest to the detection surface and wherein the step of operating the detector is carried out for verifying the presence of the first and second substances of interest in the verification solution.

* * * * *